United States Patent [19]

Lowell, Jr. et al.

[11] Patent Number: 5,028,394
[45] Date of Patent: Jul. 2, 1991

[54] CHEMICAL SENSORS

[75] Inventors: James R. Lowell, Jr.; David J. Edlund; Dwayne T. Friesen; George W. Rayfield, all of Bend, Oreg.

[73] Assignee: Bend Research, Inc.

[21] Appl. No.: 509,012

[22] Filed: Apr. 13, 1990

[51] Int. Cl.$^5$ .................... G01N 19/00; G01N 19/10; G01N 27/00

[52] U.S. Cl. ........................ 422/58; 422/57; 422/68.1; 422/82.01; 422/82.02; 436/150; 436/151; 73/23.2; 73/24.01; 73/24.06; 73/53; 73/775; 73/776

[58] Field of Search ............... 73/23.2, 24.01, 24.06, 73/53, 775, 776; 436/150, 151; 422/57, 58, 68.1, 82.01, 82.02

[56] References Cited

U.S. PATENT DOCUMENTS

| | | | |
|---|---|---|---|
| 3,343,044 | 9/1967 | King et al. ..................... | 73/24.06 X |
| 3,744,296 | 7/1973 | Beltzer .......................... | 436/151 X |
| 3,860,673 | 1/1975 | Lawrence ...................... | 528/73 X |
| 3,959,080 | 5/1976 | Orth et al. ..................... | 435/179 |
| 3,999,122 | 12/1976 | Winstel et al. ............... | 422/82.02 X |
| 4,144,227 | 3/1979 | Giuffre et al. ................ | 525/344 X |
| 4,299,895 | 11/1981 | Archie, Jr. et al. .......... | 430/17 |
| 4,352,884 | 10/1982 | Nakashima et al. .......... | 422/57 X |
| 4,681,855 | 7/1987 | Huang ............................ | 422/90 X |
| 4,746,577 | 5/1988 | Panteus et al. ................ | 524/254 X |
| 4,816,130 | 3/1989 | Karakelle et al. ............. | 436/68 X |
| 4,824,640 | 4/1989 | Hildenbrand et al. ......... | 422/58 X |
| 4,833,014 | 5/1989 | Linder et al. ................. | 428/310.5 X |

Primary Examiner—Robert J. Warden
Assistant Examiner—Stephanie Blythe
Attorney, Agent, or Firm—Chernoff, Vilhauer, McClung & Stenzel

[57] ABSTRACT

Sensors responsive to small changes in the concentration of chemical species are disclosed, comprising (a) a mechanochemically responsive polymeric film capable of expansion or contraction in response to a change in its chemical environment, operatively coupled to (b) a transducer capable of directly converting said expansion or contraction to a measurable electrical response.

36 Claims, 3 Drawing Sheets

CHEMICAL SENSORS

The government has rights in this invention pursuant to Contract No. DE-AC03-87ER80514 awarded by the Department of Energy and Contract No. 68D80070 awarded by the Environmental Protection Agency.

BACKGROUND OF THE INVENTION

Fast and accurate monitoring of the pH and toxic metals content of industrial waste streams and of waterways has become a task of paramount importance in current efforts to maintain the quality of the environment. Commercially available sensors for toxic metal ions are limited to ion-selective electrodes (ISEs) for detecting Ag(I), Cd(II), Cu(II), and Pb(II). Such devices are based on a potentiometric measurement, and their accuracy is affected by numerous interfering agents. Furthermore, ISEs are fragile, respond slowly, can be used only in aqueous solutions, are subject to fouling, and require frequent calibration. For these reasons ISEs are not suitable for widespread use in pollution-control systems, and most operators must therefore rely on costly and time-consuming off-site laboratory analyses to determine if a waste stream or groundwater contains excessive levels of toxic materials. Belyakov, in 17 *Soviet Automatic Control* 34 (1984), discloses several theoretical sensors comprising fibers, granules or round polymer contractile films operatively coupled to mechanical transducers such as springs and pistons. In discussing the theoretical kinetics of such sensors, the author assumed that the analyte of interest carries no electrical charge.

For on-site control of waste discharge, ideally a sensor would be connected to an automatic flow shut-off valve in the effluent stream by a feedback control loop such that if levels of hydrogen or hydroxide ion or certain metals exceeded preset limits, the sensor would signal the valve to interrupt discharge, thus preventing excessive release to the environment. In cases where contamination of the environment had already occurred or was suspected of occurring, remotely placed sensors could be used to continuously monitor the groundwater to provide a detailed map of the extent of contamination. For such applications a sensor must be sensitive to the analyte, must respond quickly to changes in the analyte concentration, must have a relatively long life, and must not require frequent calibration. These needs are met by the chemical sensor of the present invention.

Many polymers are known to be capable of exhibiting a physical response, such as expansion or contraction, to a change in the polymer's chemical environment, such as a change in the concentration of a given chemical species, usually as a result of chemical or physical interaction with the species. This capability is often referred to as "mechanochemical" responsiveness. Poly(methacrylic acid) (PMAA), crosslinked either with divinylbenzene or by esterification, is known to undergo volume expansions of up to 300% on conversion from the acid form to the polyanion form. Such expansion, which is reversible upon addition of mineral acid, has been explained on the basis of conformation changes in the polymer. The electrically neutral polyacid form consists of tightly coiled polymer chains. However, when the polymer is converted to the polyanion form, it has been theorized that electrostatic repulsion between negatively charged carboxylate groups results in full extension of the polymer chains and in the observed 300% expansion. See Kuhn et al., 7 *Experientia* 1 (1951).

This expansion/contraction response of methacrylic acid polymer is not limited to the reaction with hydrogen and hydroxide ions. PMAA and poly(acrylic acid) (PAA) have been shown to form complexes with transition metal and alkaline earth cations. See Gregor et al., 59 *J. Phys. Chem.* 34 (1955). PAA complexed more strongly than did PMAA, and both formed stronger complexes than did glutaric acid, their monomeric analog. The complexation constant varied with the metal and its valence; transition metals generally yielded stronger complexes than did alkaline earth metals, and divalent and trivalent ions complexed more strongly than did monovalent ions. See Osada, 18 *J. Polym. Sci.* 281 (1980). The experimental results suggest that the complexes involve two carboxylate ions per metal ion over a wide range of pH values. See Mandel et al., 2 *J. Polym. Sci.* 2883 (1964 part A). Crosslinked polymers formed weaker complexes than did linear polymers. Gregor et al., 59 *J. Phys. Chem.* 366 (1955). That the complexation of these metal ions by polycarboxylate anions involves a contractile response was demonstrated by the results of Osada, who used the same coiled-versus-extended-chain hypothesis to explain the increase in permeability observed in PMAA-grafted porous poly(vinyl alcohol) (PVA) membranes upon exposure to copper(II) salt solutions.

It has now been found that very sensitive, fast and long-lasting sensors for chemical species can be prepared by coupling an appropriate electrical transducer with thin polymer films that undergo a dimensional change in response to changes in the concentration of the species of concern.

SUMMARY OF THE INVENTION

The present invention comprises a two-element chemical sensor consisting of (a) a mechanochemically responsive polymeric film capable of expansion or contraction in response to a change in its chemical environment, operatively coupled to (b) a transducer capable of directly converting said expansion or contraction to a measurable electrical response.

DETAILED DESCRIPTION OF THE INVENTION

According to the present invention, there is provided a simple, economical, fast, accurate and reliable means of measuring changes in the concentration of chemical species in both aqueous and nonaqueous environments.

Figure 1A:
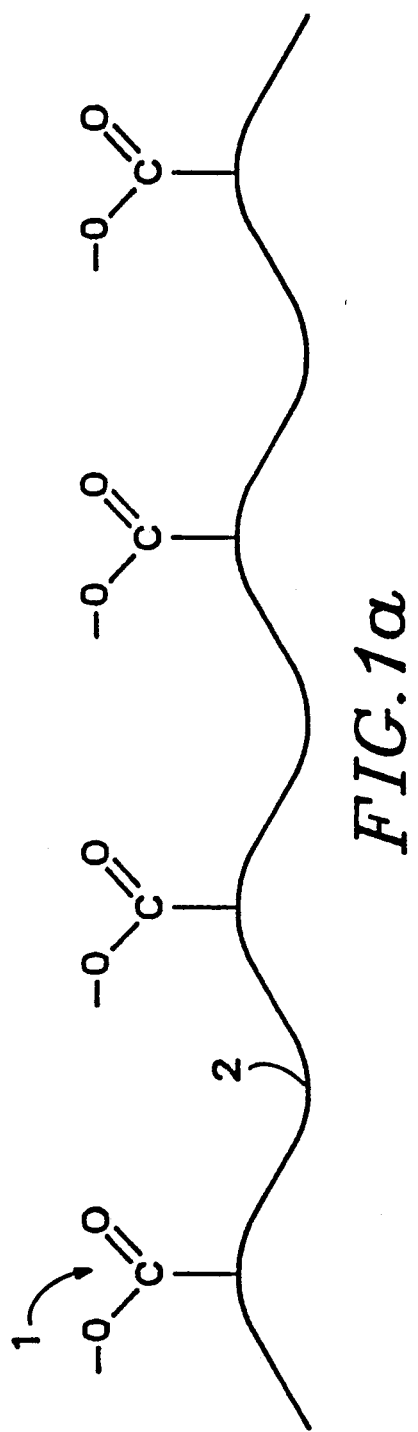
FIGS. 1a and 1b are schematic illustrations of an exemplary mechanochemical response in a polymer film of the sensor of the present invention.
Figure 1B:
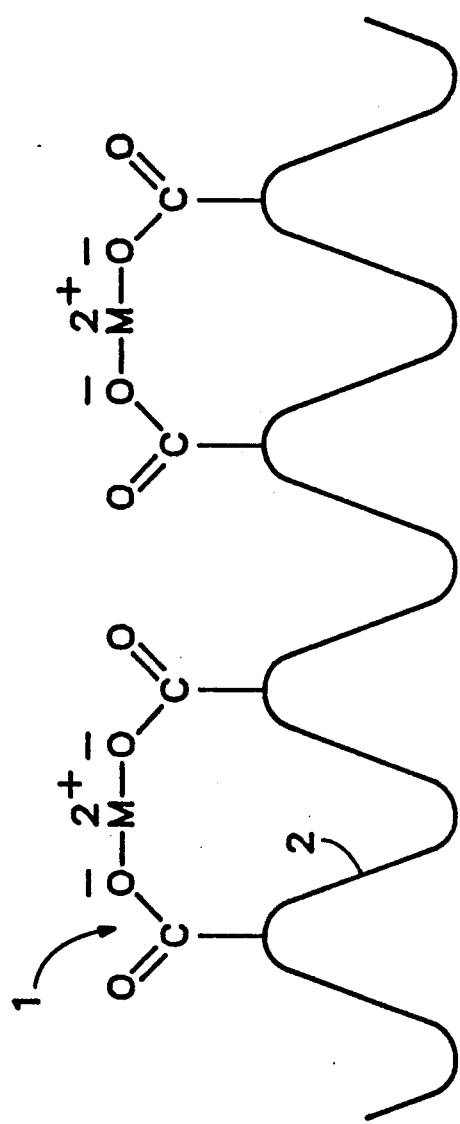

FIG. 1a shows a schematic of an exemplary mechanochemically responsive polymeric film containing carboxylate functional groups 1 in pendant positions covalently bonded to the polymer backbone 2 prior to coordination with metal ions. FIG. 1b shows the same film after coordination with metal ions M, which causes a contraction of the film. Generally speaking, in order to be capable of an expansion or contractile response, the sensing element should be wettable by, and preferably swellable by, a solution of the analyte of interest. Other functional groups besides carboxylate that may be included in the mechanochemically responsive sensing element portion of the sensor of the present invention include those that are capable of coordinating or otherwise interacting with hydrogen ions and weak acids, hydroxide ions and weak bases, metal ions or other analytes of interest. Such other functional groups include an aldehyde, an amine, an imine, an amide, an imide, a carbamate, an ester, an ether, a hydroquinone, a hydroxy, a ketone, a lactam, a lactone, a nitrile, a phosphate, a phosphine, a phosphite, a pyridine, an alkylated pyridine, a sulfone, a sulfoxide, a thiol, a thioamide, a thioester, a thioether, a thiourea, a urea, a urethane, and heterocycles containing oxygen, nitrogen or sulfur hetero atoms. The mechanochemically responsive polymeric film may contain more than one species of functional group and, in this manner, may be "tuned" to fit a particular application where the presence of more than one chemical species is to be detected or, owing to the particular chemical environment, detection of the species of interest requires the presence of more than one type of functional group.

Although FIGS. 1a and 1b show the functional group 1 covalently bonded to the polymer backbone 2 in pendant positions, such functional groups may also be part of the repeating unit of the mechanochemically responsive polymeric film or the polymeric film may be doped with the functional group(s). By "doped" is meant physically absorbed onto or into the mechanochemically responsive polymeric film.

Particularly preferred sensing element polymers include polyethyleneimine (PEI), poly(acrylic acid) (PAA) and poly(alkylacrylic acid) such as poly(methacrylic acid) (PMAA). Crosslinking such polymers imparts resilience, durability and dimensional stability to the sensing element, and is preferably accomplished by conventional methods with 0.01 to 0.2 mol of crosslinking reagent per polymer repeating unit. Exemplary crosslinking reagents are polyamines such as ethylenediamine, diethylenetriamine, 1,6-hexanediamine and phenylenediamine; polyols such as glycerol, ethylene glycol, sorbitol, mannitol, scyllitol and inisotols (d-,l- and myo-); multifunctional acid halides such as adipoyl chloride, isophthaloyl chloride, malonyl chloride, terephthaloyl chloride and trimesoyl chloride; and multifunctional isocyanates such as tolylene diisocyanate (TDI), phenylene diisocyanate, methylene-bis(phenylisocyanate) and poly[methylene-bis(phenylisocyanate)]. In addition, grafted polymers having pendant functional groups such as carboxylate, amine, quaternary amine and sulfonate grafted to polymers such as polyethylene, polypropylene, polysulfone, polyethersulfone, polyamide, polyetherimide, polyester and poly(vinylidene fluoride) make desirable sensing elements for use in the sensors of the present invention. A preferred series of commercially available grafted polymers is the Raipore ® series from RAI Research Corporation of Long Island, N.Y., including Raipore ® ADM-4000 (a tertiary amine-grafted polyethylene), Raipore ® 5035 (a quaternized vinylbenzylamine-grafted polyethylene), Raipore ® R-1010 (a sulfonate-grafted polyethylene), and Raipore ® BDM-10 (a carboxylate-grafted polyethylene).

Figure 2:
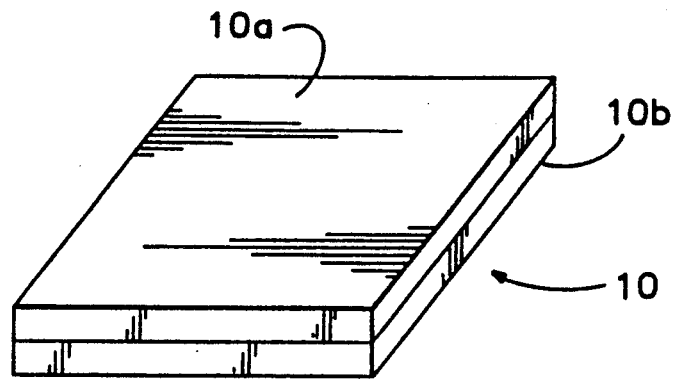
FIG. 2 is a schematic isometric drawing of an exemplary sensor of the present invention, consisting of a mechanochemically responsive polymer film and an electrical transducer.

FIG. 2 shows a schematic of an exemplary sensor 10 comprising the mechanicochemically responsive polymeric film sensing element 10a and a transducer 10b. In general the sensing element portion 10a of the sensor should be fairly thin, on the order of 1–20 mils thick, in order to minimize the time required for diffusion of the analyte into the bulk of the sensing element and to maximize its flexibility and thus its ability to efficiently transfer expansion or contraction to the transducer 10b. Ideally, the sensing element should be integral with the transducer element, through fusing, adhesion or bonding with an adhesive between the sensing element and the transducer.

Conventional polymer fabrication methods may be used in preparing the sensing element; two methods are particularly preferred, i.e., casting and interfacial polymerization. One version of the casting method uses a solution of the desired polymer cast in a very thin film, which then is allowed to evaporate, depositing the polymer on the transducer support. Alternatively, a solution of complementary monomers may be cast as a thin film on the support. Polymerization of the monomers may then proceed spontaneously to be induced by removal of the solvent; e.g., azeotropic dehydration will tend to drive a condensation polymerization to completion by elimination of water. Both casting methods generally result in adhesion of the polymer film to the transducer support. In the interfacial polymerization technique, a thin film of a solution of a first reagent (a multifunctional monomer) is applied to the transducer support, then a second solution (in an immiscible solvent) of a monomer containing complementary functional groups that are reactive with the first reagent in a condensation reaction is applied to the support. Polymerization occurs at the interface between the two solutions to yield a very thin, defect-free film.

The fundamental requirement of the transducer element of the sensor is that it be capable of directly converting to a measurable electrical response the expansion or contraction transmitted to it by the sensing element. Suitable transducers are strips of piezoelectric material and strain gauges, the latter including metal foil-types, semiconductor types and capacitance devices.

Figure 3A:
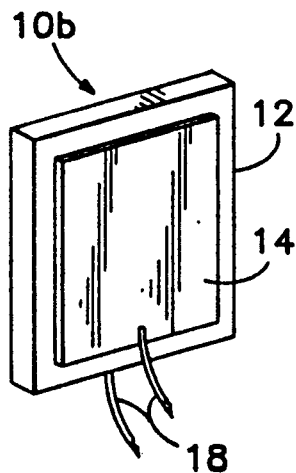
FIGS. 3a and 3b are schematic drawings of both sides of an exemplary polymeric piezoelectric transducer of the sensor of the present invention.
Figure 3B:
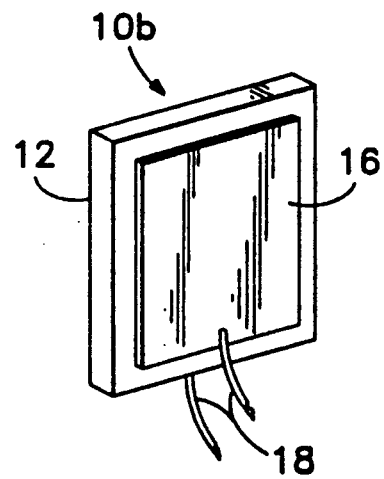

Piezoelectric materials are known to undergo a change in surface charge density upon deformation so that, in principle, if electrodes are attached to the two surfaces of a planar strip of such material, a measurable voltage occurs upon expansion or contraction of the material. Thus, if piezoelectric material is coupled to a mechanochemically responsive analyte-sensitive element of the type described herein, a measurable voltage can be produced in response to a change in the concentration of an analyte of interest. A particularly preferred piezoelectric material is extruded and polarized poly(vinylidene fluoride) (PVDF) that is commercially available as "Kynar®" from the Pennwalt Corporation of King of Prussia, Pa. After extrusion, the PVDF Kynar® film contains nonpolar alpha- and polar beta-crystallite phases. The film is then stretched at 80° to 110° C., metallized with a conductive metal such as palladium or silver by vacuum deposition or screen printing, then polarized by subjecting it to an intense electric field at 80° to 100° C., followed by cooling it within the applied field. A schematic drawing of a Kynar® piezoelectric transducer 10b is shown in FIGS. 3a and 3b as comprising a PVDF substrate 12 having a working electrode 14 on one side of the substrate and a common electrode 16 on the other side, and leads 18 for connection to an electrical response measuring device such as a voltmeter. Such a transducer may be modified to incorporate a reference electrode with the working electrode on the same side of the substrate; the signal from the reference electrode may be subtracted from the working electrode signal to remove background electrical noise from the sensor response.

Figure 6:
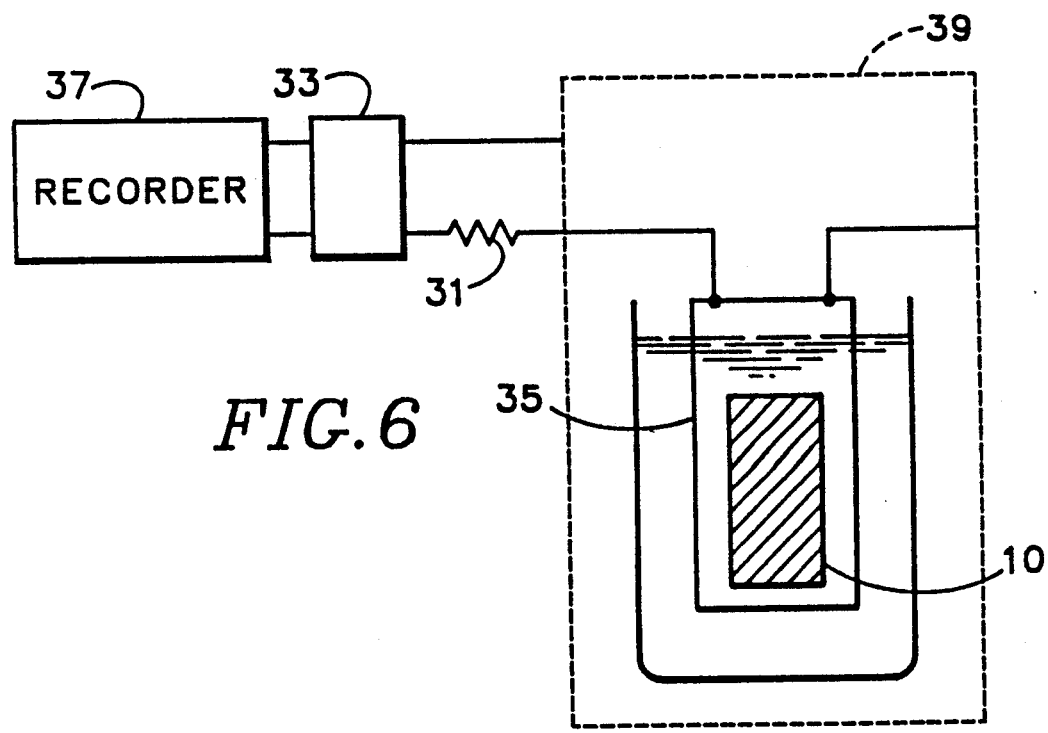
FIG. 6 is a schematic drawing of an exemplary electrical circuit for use in measuring changes in the resistance of a piezoelectric transducer of the present invention.

A circuit for measuring the voltage produced by the piezoelectric Kynar® transducer is shown in FIG. 6. The large resistor 31 ($10^8$ ohm) prevents the piezoelectric strip from discharging too rapidly. The 10 amplifier 33 simply amplifies the voltage produced by the piezoelectric sensor 10 immersed in analyte solution 35 to a value (0.1-10 V) that is conveniently displayed on a recorder entire circuit.

Figure 4:
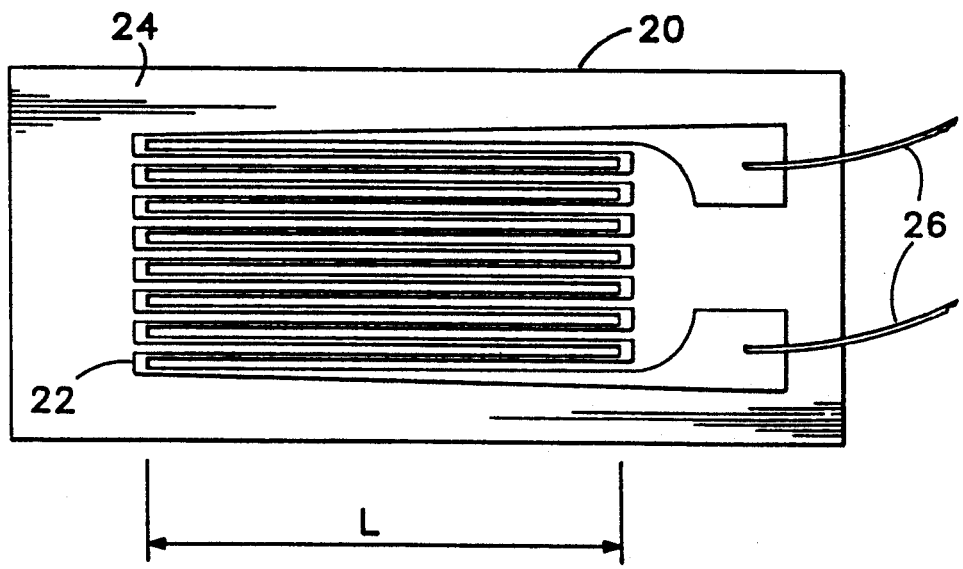
FIG. 4 is a schematic drawing of an exemplary metal foil strain gauge transducer of the sensor of the present invention.
Figure 7:
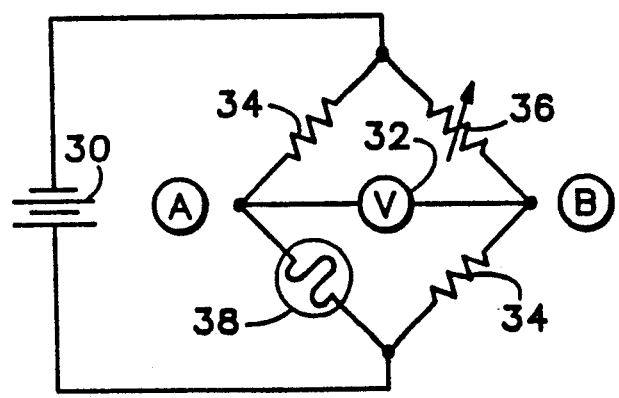
FIG. 7 is a schematic drawing of an exemplary Wheatstone bridge circuit for use in measuring changes

Strain gauges are well known and are preferably either of the thin metal foil type or the semiconductor type. A metal foil strain gauge is shown schematically in FIG. 4 as structure 20 having a serpentine conductive metal foil grid 22 on a nonconductive substrate 24, with leads 26 to the grid 22. When the strain gauge is expanded or contracted along the L axis, the electrical resistance of the grid will increase or decrease, respectively, according to the equation $$\Delta R/R = F(\Delta L/L)$$

where R is the initial resistance, $\Delta R$ is the change in resistance, F is a dimensionless constant called the gauge factor, L is the initial length of the gauge, and $\Delta L$ is the change in the length of the gauge. Small changes in electrical resistance of such strain gauges are readily measured, for instance, with a Wheatstone bridge circuit, a simple form of which is pictured schematically in FIG. 7, wherein there is shown a DC power source 30, a DC voltmeter 32, fixed resistors 34, a variable resistor 36, and a strain gauge 38. The Wheatstone bridge circuit measures a small resistance change as an imbalance in the voltage potential between points A and B; the circuit derives its sensitivity from the fact that small potential differences between points A and B can be measured indirectly, but very precisely.

The semiconductor strain gauge is based on the piezoresistive effect in certain semiconductor materials such as silicon and germanium. Semiconductor gauges have elastic behavior and can be produced to have either positive or negative resistance changes when strained. They can be made physically small while still maintaining a high terminal resistance. Semiconductor gauges exhibit a high sensitivity to strain but the change in resistance with strain is nonlinear. Their resistance and output are temperature-sensitive and the high output, resulting from changes in resistance as large as 10-20%, can cause measurement problems when using the devices in a bridge circuit. However, mathematical corrections for the temperature sensitivity, the nonlinearity of output, and the nonlinear characteristics of the bridge circuit (if used), can be made automatically when using computer-controlled instrumentation to measure strain with semiconductor gauges. Both metal foil strain gauges and semiconductor strain gauges are commercially available from Omega Engineering of Stamford, Conn.

In the Examples which follow, it should be noted that, in those cases where hydrogen ion concentration is measured in aqueous environments, hydroxide ion concentration is calculable from the mathematical relationship $[H^+][OH^-] = 10^{-14}$, and thus also measurable. In a nonaqueous environment, the sensor would have to be first calibrated by measuring the electrical response to known concentration of hydroxide ion.

EXAMPLE 1

A sensor that utilized a Kynar® piezoelectric strip transducer of the type shown in FIGS. 3a and 3b was prepared by mixing 1.0 g (0.023 unit-mol, where a unit-mol is a gram-molecular-weight of a repeating monomer unit in a polymer solution) of poly(ethylenimine) (PEI) and 0.05 g ($2.9 \times 10^{-4}$ mol) of 2,4-tolylenediisocyanate (TDI) to produce a soft, gel-like polymer mixture. The gel was pressed onto a 28 micron-thick Kynar® piezoelectric PVDF strip measuring 17×40 mm, after which the strip was heated at 90° to 95° C. until the PEI gel was quite stiff. Silver electrodes screen printed on each surface of the PVDF film permitted electrical connections to the sensor. Using a circuit of the type shown in FIG. 6, the so-fabricated sensor gave an electrical response comprising a voltage change ranging from 1500 mV to 3000 mV, when immersed in aqueous solutions of pH between 4 and 8.5, that was proportional to the change in pH, as shown in Table 1.

TABLE 1

| pH | Response (mV) |
|---|---|
| 8.0 | 3000 |
| 7.5 | 2550 |
| 6.5 | 2230 |
| 5.5 | 1920 |
| 4.5 | 1675 |
| 4.0 | 1500 |

EXAMPLE 2

A sensor was prepared by coating the same size and type piezoelectric strip as in Example 1 with a film of amide-crosslinked PMAA. A silicone rubber dam, capable of holding approximately 3 ml of liquid, was placed around the periphery of the piezoelectric strip. A 2 to 3 ml quantity of a 0.35 unit-molar aqueous solution of PMAA containing $1.7 \times 10^{-3}$ mol of 1,6-hexanediamine per liter and 0.1% poly(ethylene glycol) (PEG) was placed on the piezoelectric strip inside the dam. The water was evaporated at 90° to 95° C., resulting in the formation of a thin amide-crosslinked PMAA film on the piezoelectric strip. Using the same type of measuring device as in Example 1, the so-fabricated sensor gave an electrical response ranging from 250 mV at pH 6.5 to 860 mV at pH 2.5 when immersed in acetonitrile solutions of HCl, as shown in Table 2.

TABLE 2

| pH* | Response (mV) |
| --- | --- |
| 6.5 | 250 |
| 5.5 | 350 |
| 4.5 | 750 |
| 3.5 | 825 |
| 2.5 | 860 |

*Calculated

EXAMPLE 3

A hydrogen ion sensor was prepared in the same manner as in Example 2 by coating the same size and type of piezoelectric-film transducer with the polymer formed in nitromethane solution by reaction of the acid chloride of PMAA with glycerol. The response to changes in hydrogen-ion concentration in nonaqueous (acetonitrile) solutions with this sensor was similar to the response of the sensor of Example 2, as shown in Table 3.

TABLE 3

| pH* | Response (mV) |
| --- | --- |
| 6.5 | 250 |
| 5.5 | 350 |
| 4.5 | 750 |
| 3.5 | 825 |
| 2.5 | 860 |

*Calculated

EXAMPLE 4

The PMAA-coated sensor of Example 2 was also responsive to changes in the concentration of Cu(II) in aqueous solutions thereof (in the form of $CuSO_4$), as shown in Table 4.

TABLE 4

| [Cu(II)] (ppb) | Response (mV) |
| --- | --- |
| 0.6 | 50 |
| 6.0 | 100 |
| 60 | 200 |
| 600 | 500 |
| 60,000 | 1300 |

EXAMPLE 5

The PMAA-coated sensor of Example 3 was identically responsive to changes in the concentration of aqueous Cu(II) as was the sensor of Example 2.

EXAMPLE 6

The PMAA-coated sensor of Example 2 was also responsive to changes in the concentration of Cr(III) in aqueous solutions thereof (in the form of $CrCl_3$), as shown in Table 5.

TABLE 5

| [Cr(III)] (ppb) | Response (mV) |
| --- | --- |
| 2.6 | 50 |
| 26 | 60 |
| 260 | 130 |
| 2600 | 260 |
| 26,000 | 710 |

EXAMPLE 7

The PMAA-coated sensor of Example 3 was identically responsive to changes in the concentration of aqueous Cr(III) as was the sensor of Example 3.

EXAMPLE 8

A sensor prepared in substantially the same manner as in Example 1 with the TDI-crosslinked PEI being doped after heating by the addition of 0.1 to 0.3 ml of the beta-diketone LIX 860 to the surface of the sensor, the doping agent being absorbed into the mechanochemically responsive polymer film. This sensor was responsive to changes in the concentration of Fe(II) and Fe(III) in aqueous solutions thereof (in the form of $FeSO_4 \cdot (NH_4)_2SO_4 \cdot 6H_2O$ and $FeCl_3$, respectively). As shown in Table 6 the sensor was much more responsive to Fe(III) than to Fe(II).

TABLE 6

| Metal Ion | [M] (ppm) | Response (mV) |
| --- | --- | --- |
| Fe(II) | 780 | 400 |
| Fe(III) | 780 | 1200 |

EXAMPLE 9

The PEI-coated sensor of Example 1 was also responsive to changes in the concentration of Cr(III) in aqueous solutions thereof (in the form of $CrCl_3$), as shown in Table 7.

TABLE 7

| [Cr(III)] (ppb) | Response (mV) |
| --- | --- |
| 260 | 100 |
| 2600 | 275 |
| 26,000 | 450 |

EXAMPLES 10-26

Figure 5:
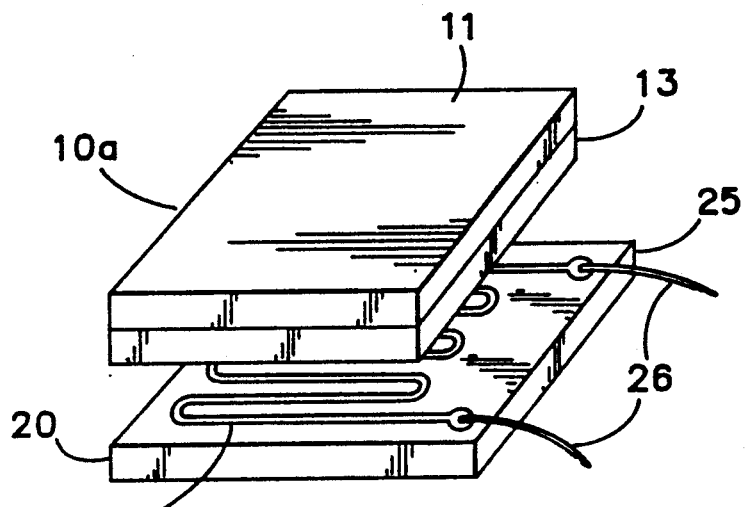
FIG. 5 is a schematic exploded view of an exemplary sensor, of the present invention, comprising a mechanochemically responsive polymer film and a strain gauge transducer.

Sensors of substantially the design shown in FIG. 5 were prepared by bonding 2×2 cm pieces of carboxylate- and tertiary amine-grafted polyethylene films 11 2 mil-thick (Raipore ® BDM-10 and ADM-4000, respectively) to metal foil strain gauge transducers 20 that had been prepared by sputtering a Pd/Au alloy in a 1.5×1.5 cm serpentine grid pattern 22 onto 2 mil-thick 2×2 cm sheets of polyurethane 25 and attaching thin copper wire leads 26 to each end of the grid with conductive silver epoxy. Bonding was accomplished by first applying a thin coating of amine functional group-containing silicone polymer 13 (GP-134 by Genesee Polymers Corp. of Flint, Mich.) to the Raipore ® polymer film, allowing it to cure, swelling it in water, blotting it dry, coating it with a general purpose silicone adhesive, and then joining the Raipore ® polymer film 11 to the strain gauge transducer 20. A Wheatstone bridge circuit of the type shown in FIG. 7 was used to detect changes in the resistance of the strain gauge, expressed as a voltage imbalance in the circuit. Size changes of the Raipore ® polymer films varied from about 0.5% to about 15.5%, in response to changes in the concentration of the metal ions Ba(II), Cd(II), Cr(III) and Cr(VI) in the form of aqueous solutions of $BaCl_2$, $CdSO_4$, $CrCl_3$ and $Na_2CrO_4$. Raipore ® BDM-10 films were used in connection with measuring the concentration of all ions except Cr(VI), in which case Raipore ® ADM-4000 was used.

The variance of the electrical response with metal ion concentration was as shown in Table 8.

TABLE 8

| Ex. No. | Metal Ion | [M] (ppm) | Response (mV) |
|---|---|---|---|
| 10 | Ba(II) | 13 | 1.1 |
| 11 | " | 10 | 0.98 |
| 12 | " | 7.0 | 0.74 |
| 13 | " | 3.5 | 0.54 |
| 14 | " | 0.7 | 0.04 |
| 15 | Cd(II) | 5.5 | 0.35 |
| 16 | " | 3.0 | 0.21 |
| 17 | " | 1.2 | 0.09 |
| 18 | " | 0.6 | 0.05 |
| 19 | Cr(III) | 2.0 | 0.96 |
| 20 | " | 1.0 | 0.65 |
| 21 | " | 0.5 | 0.47 |
| 22 | " | 0.03 | 0.40 |
| 23 | Cr(VI) | 20 | 0.26 |
| 24 | " | 15 | 0.19 |
| 25 | " | 10 | 0.17 |
| 26 | " | 5.0 | 0.10 |

Based upon the results shown in Table 8, the calculated limits of detection of the sensors of Examples 10–26 are shown in Table 9.

TABLE 9

| Analyte | Limits of Detection (ppm) | |
|---|---|---|
| | Minimum | Maximum |
| Ba(II) | 0.67 | >13.4 |
| Cd(II) | 0.56 | >5.6 |
| Cr(III) | 0.025 | >2.0 |
| Cr(VI) | 5.0 | >20.0 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A chemical sensor comprising (a) a mechanochemically responsive polymeric film capable of dimensional expansion or contraction in response to a change in its chemical environment, adhered to (b) a transducer capable of directly converting said dimensional expansion or contraction to an electrical response.

2. The sensor of claim 1 wherein said mechanochemically responsive polymeric film contains at least one functional group, said at least one functional group being selected from an aldehyde, an amine, an imine, an amide, an imide, a carbamate, a carboxylate, an ester, an ether, a hydroquinone, a hydroxy, a ketone, a lactam, a lactone, a nitrile, a phosphate, a phosphine, a phosphite, a pyridine, an alkylated pyridine, a sulfone, a sulfoxide, a thiol, a thioamide, a thioester, a thioether, a thiourea, a urea, a urethane, and heterocycles containing oxygen, nitrogen or sulfur hetero atoms.

3. The sensor of claim 2 wherein said mechanochemically responsive polymer film is doped with said at least one functional group.

4. The sensor of claim 2 wherein said at least one functional group is covalently bonded to the polymer backbone of said mechanochemically responsive polymeric film.

5. The sensor of claim 4 wherein said at least one functional group is in pendant positions on said polymer backbone.

6. The sensor of claim 4 wherein said at least one functional group is part of the repeating unit of said polymer backbone.

7. The sensor of claim 1 wherein said mechanochemically responsive polymeric film is selected from polyethyleneimine, poly(acrylic acid) and poly(alkylacrylic acid).

8. The sensor of claim 1 wherein said mechanochemically responsive polymeric film is crosslinked with 0.01 to 0.2 mol crosslinking reagent per polymer repeating unit.

9. The sensor of claim 8 where said crosslinking reagent is selected from the group consisting of a polyamine, a polyol, an acid chloride and an isocyanate.

10. The sensor of claim 9 wherein said crosslinking reagent is a polyamine and said polyamine is selected from the group consisting of ethylenediamine, diethylenetriamine, hexamethylenediamine, 1,6-hexanediamine and a phenylenediamine.

11. The sensor of claim 9 wherein said crosslinking reagent is a polyol and said polyol is selected from the group consisting of glycerol, ethylene glycol, sorbitol, mannitol, scyllitol and inisotols.

12. The sensor of claim 9 wherein said crosslinking reagent is an acid chloride and said acid chloride is selected from the group consisting of adipoyl chloride, isophthaloyl chloride, malonyl chloride, terephthaloyl chloride and trimesoyl chloride.

13. The sensor of claim 9 wherein said crosslinking reagent is an isocyanate and said isocyanate is selected from the group consisting of tolylene diisocyanate, a phenylene diisocyanate, methylene bis-(phenylisocyanate) and poly.

14. The sensor of claim 1 wherein said mechanochemically responsive polymer film comprises a functional group-grafted copolymer wherein the functional group is selected from carboxylate, sulfonate and amine.

15. The sensor of claim 14 wherein the polymer to which said functional group is grafted is selected from polyethylene, polypropylene, poly(vinylidenefluoride) and polysulfone.

16. The sensor of claim 1 wherein said transducer is selected from a piezoelectric material and a strain gauge.

17. The sensor of claim 16 wherein said piezoelectric material is a piezoelectric polymer.

18. The sensor of claim 17 wherein said piezoelectric polymer is polarized poly(vinylidenefluoride).

19. The sensor of claim 16 wherein said strain gauge is selected from a metal foil strain gauge and a semiconductor strain gauge.

20. The sensor of claim 1 wherein the change in chemical environment is a change in hydrogen ion concentration.

21. The sensor of claim 1 wherein the change in chemical environment is a change in the concentration of a weak acid.

22. The sensor of claim 20 or 21 wherein the chemical environment is aqueous.

23. The sensor of claim 20 or 21 wherein the chemical environment is nonaqueous.

24. The sensor of claim 1 wherein the change in chemical environment is a change in hydroxide ion concentration.

25. The sensor of claim 1 wherein the change in chemical environment is a change in the concentration of a weak base.

26. The sensor of claim 23 or 24 wherein the chemical environment is aqueous.

27. The sensor of claim 23 or 24 wherein the chemical environment is nonaqueous.

28. The sensor of claim 1 wherein the change in chemical environment is a change in transition metal ion concentration.

29. The sensor of claim 28 wherein the transition metal ion is Cd(II).

30. The sensor of claim 28 wherein the transition metal ion is Cr(III).

31. The sensor of claim 28 wherein the transition metal ion is Cr(VI).

32. The sensor of claim 28 wherein the transition metal ion is Cu(II).

33. The sensor of claim 28 wherein the transition metal ion is Fe(II).

34. The sensor of claim 28 wherein the transition metal ion is Fe(III).

35. The sensor of claim 28 wherein the mechanochemically responsive polymeric film is doped with a beta-diketone.

36. The sensor of claim 1 wherein the change in chemical environment is a change in Ba(II) concentration.

* * * * *